(12) United States Patent
Gardner et al.

(10) Patent No.: US 12,140,530 B2
(45) Date of Patent: Nov. 12, 2024

(54) BIOMARKER VALUE CALCULATION METHOD

(71) Applicant: ROCKLEY PHOTONICS LIMITED, Altrincham (GB)

(72) Inventors: Craig Gardner, Belmont, MA (US); Philip Perea, Aliso Viejo, CA (US)

(73) Assignee: Rockley Photonics Limited, Altrincham (GB)

( * ) Notice: Subject to any disclaimer, the term of this patent is extended or adjusted under 35 U.S.C. 154(b) by 0 days.

(21) Appl. No.: 17/937,444

(22) Filed: Sep. 30, 2022

(65) Prior Publication Data

US 2023/0104416 A1 Apr. 6, 2023

Related U.S. Application Data

(60) Provisional application No. 63/291,282, filed on Dec. 17, 2021, provisional application No. 63/251,444, filed on Oct. 1, 2021.

(51) Int. Cl.
*G01N 21/27* (2006.01)
*A61B 5/00* (2006.01)
(Continued)

(52) U.S. Cl.
CPC .......... *G01N 21/274* (2013.01); *A61B 5/0075* (2013.01); *A61B 5/14551* (2013.01);
(Continued)

(58) Field of Classification Search
CPC ............... G01N 21/274; G01N 21/359; A61B 5/0075; A61B 5/14551; A61B 5/7267;
(Continued)

(56) References Cited

U.S. PATENT DOCUMENTS

| 8,571,618 | B1 | 10/2013 | Lamego et al. | |
| 2004/0242980 | A1* | 12/2004 | Kiani | A61B 5/14535 600/326 |
| 2005/0277818 | A1* | 12/2005 | Myers | A61B 5/14551 600/323 |
| 2014/0051953 | A1* | 2/2014 | Lamego | A61B 5/14532 600/316 |

(Continued)

FOREIGN PATENT DOCUMENTS

| WO | WO 2003/010510 A3 | 2/2003 | |
| WO | WO-03010510 A2 * | 2/2003 | ......... A61B 5/14532 |
| WO | WO-2019161411 A1 * | 8/2019 | ........... A61B 5/0075 |

OTHER PUBLICATIONS

Bickler, P. E. et al., "Effects of Skin Pigmentation on Pulse Oximeter Accuracy at Low Saturation", Anesthesiology, Apr. 2005, pp. 715-719, vol. 102, No. 4, American Society of Anesthesiologists, Inc. Lippincott Williams & Wilkins, Inc.

(Continued)

*Primary Examiner* — Dominic J Bologna
(74) *Attorney, Agent, or Firm* — Lewis Roca Rothgerber Christie LLP

(57) ABSTRACT

A computer-implemented method to improve the accuracy of a calculation of a biomarker value from a spectral measurement. The computer-implemented method comprises receiving a primary spectral measurement from a primary detector, receiving, a secondary measurement from a secondary detector, and calculating a value of the biomarker using a biomarker algorithm. The biomarker algorithm takes an input from the primary spectral measurement and a calibration parameter from the secondary measurement.

21 Claims, 9 Drawing Sheets

(51) Int. Cl.
   *A61B 5/01*      (2006.01)
   *A61B 5/145*     (2006.01)
   *A61B 5/1455*    (2006.01)
   *G01J 3/10*      (2006.01)
   *G01J 3/28*      (2006.01)
   *G01N 21/359*    (2014.01)

(52) U.S. Cl.
   CPC .............. *A61B 5/7267* (2013.01); *G01J 3/10* (2013.01); *G01N 21/359* (2013.01); *A61B 5/01* (2013.01); *A61B 5/14532* (2013.01); *A61B 5/14546* (2013.01); *G01J 2003/2866* (2013.01)

(58) Field of Classification Search
   CPC ................. A61B 5/01; A61B 5/14532; A61B 5/14546; G01J 3/10; G01J 2003/2866
   See application file for complete search history.

(56) References Cited

U.S. PATENT DOCUMENTS

| | | | |
|---|---|---|---|
| 2016/0069743 A1* | 3/2016 | McQuilkin | A22B 5/007 356/416 |
| 2017/0303830 A1* | 10/2017 | Klein | A61B 5/0075 |
| 2020/0397306 A1* | 12/2020 | Frank | G01J 5/10 |

OTHER PUBLICATIONS

Laxminarayan, S. et al., "Individualized estimation of human core body temperature using noninvasive measurements", J Appl Physiol, Feb. 8, 2018, pp. 1387-1402, the American Physiological Society.
International Search Report and Written Opinion of the International Searching Authority, mailed Feb. 2, 2023, corresponding to PCT/IB2022/000562, 13 pages.

* cited by examiner

BIOMARKER VALUE CALCULATION METHOD

CROSS-REFERENCE TO RELATED APPLICATION(S)

The present application claims priority to and the benefit of U.S. Provisional Application Nos. 63/251,444, filed Oct. 1, 2021 entitled "SYSTEMS AND METHODS FOR IMPROVED SENSOR ALGORITHMS", and 63/291,282, filed Dec. 17, 2021 entitled "SYSTEMS AND METHODS FOR IMPROVED SENSOR ALGORITHMS"; the entire contents of all of the documents identified in this paragraph are incorporated herein by reference.

FIELD

One or more aspects of embodiments according to the present invention relate to a method of calculating of a biomarker value, and more particularly to a method of calculating a biomarker value from a spectral measurement.

BACKGROUND

Biomarker estimation methods exist wherein spectral data is collected from a user and subsequently used to calculate a biomarker value associated with that user. In these methods, an algorithm is applied to the spectral data, and the algorithm outputs an estimated value of the biomarker. For example, oxygen saturation estimation methods apply an algorithm to red wavelength and infrared wavelength spectral data to calculate an oxygen saturation value.

However, spectral data can be affected by user characteristics such as skin pigmentation, and environmental factors such as ambient temperature.

A need exists to improve the accuracy of existing biomarker estimation methods.

SUMMARY

Accordingly, embodiments of a first aspect of the invention provide a computer-implemented method to improve the accuracy of a calculation of a biomarker value from a spectral measurement, the computer-implemented method comprising receiving a primary spectral measurement from a primary detector, receiving a secondary measurement from a secondary detector, and calculating a value of the biomarker using a biomarker algorithm, which takes an input from the primary spectral measurement and a calibration parameter from the secondary measurement.

In this way, the computer-implemented method may increase the accuracy of biomarker value calculations which use spectral measurements, which may be variable with a factor external to the biomarker (an "external factor"). The factor external to the biomarker may be a user-specific characteristic. A user-specific characteristic may be skin pigmentation, skin thickness, BMI, subcutaneous tissue thickness, temperature of skin components such as water, amount of hemoglobin species such as carboxy-hemoglobin or met-hemoglobin, amount of bilirubin, sun damage, subcutaneous fat thickness, or amount of melanin, or a plurality of these factors in combination.

A spectral measurement may mean an electromagnetic spectral measurement. A spectral measurement may mean an optical measurement.

A biomarker may mean an indicator of a biological state or an indicator of a biological condition. A biomarker value may mean a quantification of a biomarker.

A calibration parameter may mean a parameter which provides an adjustment to the input from the primary spectral measurement such that an external factor is taken into account in the biomarker value calculation.

Optional features of the computer-implemented method will now be described. The computer-implemented method may have any one, or any combination insofar as they are compatible, of the following features.

The primary detector may be a component of a primary sensor. The primary sensor may be a component of a photonic integrated circuit (PIC). The primary sensor may further comprise a primary light source. A light source may mean an electromagnetic spectrum source, and may not be limited to an visible light source. The primary sensor may comprise a plurality of primary light sources.

The primary sensor may be configured to operate each primary light source in the plurality of primary light sources one at a time. In this way, the primary sensor may only require a single primary detector.

The primary light source may be an LED. The primary light source may be a laser.

The primary light source may be an infrared light source. Infrared light may have a wavelength in the range 700 nm to 1,000,000 nm. The primary light source may be a short-wavelength infrared (SWIR) light source. SWIR light may have a wavelength in the range 1400 nm to 3000 nm. The primary light source may be a visible light source. Visible light may have a wavelength in the range 400 nm to 700 nm. The primary light source may be a near-infrared light source. Near-infrared light may have a wavelength in the range 700 nm to 1400 nm.

The plurality of primary light sources may be suitable for creating spectra for making a PPG measurement. A PPG measurement may provide information on the content of the blood. For example, a PPG measurement may provide information on a functional oxygen saturation (Func SpO2), a fractional oxygen saturation (Frac SpO2, methemoglobin (MetHb), carboxyhemoglobin (COHb) and/or a total hemoglobin. A PPG measurement may provide information on a heart rate. In this case, the primary light sources may be collectively referred to as a PPG light source. The PPG light source may emit light in the wavelength range 600 nm to 1000 nm. The PPG light source may emit light in the wavelength range 400 nm to 1400 nm. The plurality of primary light sources may comprise an infrared light source and a red light source. The infrared light source may emit light at approximately at 940 nm. The red light source may emit light at approximately 660 nm. The plurality of primary light sources may comprise a green light source. The green light source may emit light at approximately at 527 nm. The primary light source or the plurality of primary light sources may cover a wavelength range of 560 nm to 900 nm. In this way, the primary sensor may be suitable for making spectral measurements for calculating biomarker value of functional oxygen saturation. The primary light source or the plurality of primary light sources may cover a wavelength range of 500 nm to 1000 nm. The primary light source may cover or emit light within the wavelength range of 500 nm to 900 nm. In this way, the primary sensor may be suitable for making spectral measurements for calculating a biomarker value where the biomarker is carboxyhemoglobin. The primary light source may cover or emit light within the wavelength range of 500 nm to 1200 nm. In this way, the primary sensor may be suitable for making spectral measurements for calculating a biomarker value where the biomarker is methemoglobin. The primary light source or the plurality of primary light sources may cover or emit light within a wavelength range of 450 nm to 1400 nm. In this way, the primary sensor may be suitable for making spectral measurements for calculating biomarker values including functional oxygen saturation, fractional oxygen saturation, and biomarker values where the biomarkers are methemoglobin, carboxyhemoglobin and/or total hemoglobin. The primary light source or the plurality of primary light source may cover a wavelength range of 400 to 2400 nm.

In this way a biomarker value for oxygen saturation may be calculated.

The primary light source may emit light within the waveband 1650 nm to 1780 nm. The primary light source may emit light within the waveband 2050 nm to 2380 nm. The primary light source or the plurality of primary light sources may cover a wavelength range of approximately 1650 nm to 1780 nm. The primary light source or the plurality of primary light sources may cover a wavelength range of approximately 2050 nm to 2380 nm.

In this way, a biomarker value for glucose concentration may be calculated.

The primary light source may emit light within the waveband 1280 nm to 1644 nm, 1290 nm to 1654 nm, 1290 nm to 2382 nm, or 1000 nm to 2500 nm. The primary light source or the plurality of primary light sources may cover a wavelength range of approximately 1280 nm to 1644 nm, 1290 nm to 1654 nm, 1290 nm to 2382 nm or 1000 nm to 2500 nm.

In this way, a biomarker value for temperature may be calculated.

The primary detector may be an infrared detector. The primary detector may be a short-wavelength infrared (SWIR) detector. The primary detector may be a near-infrared detector. The primary detector may be a visible light detector. A given waveband detector may mean a detector which is able to detect light in that given waveband.

The primary detector may be a detector suitable for detecting an AC spectral measurement. In this case, the primary detector may be referred to as a PPG detector. The primary detector may be suitable for detecting a DC spectral measurement. The primary detector may include a red waveband detector and an infrared waveband detector. The red waveband detector and the infrared waveband detector may be the same detector. The primary detector may be suitable for detecting light across the wavelength range 400 to 2400 nm.

A sensor comprising a given waveband light source and a given waveband detector may be referred to as a given waveband sensor. A sensor comprising a PPG light source and a PPG detector may be referred to as a PPG sensor. Measurements made by a PPG sensor may be referred to as PPG measurements.

The primary detector may be a photodetector. The photodetector may be a silicon photodetector. The primary detector may be a spectrometer. The primary detector may be a spectrophotometer.

The computer-implemented method may comprise receiving a plurality of primary spectral measurements from a respective plurality of primary detectors. Each of the plurality of primary photodetectors may be the same type of photodetector. Each of the plurality of primary photodetectors may be located at a different distance from the primary light source.

In this way, each of the plurality of primary spectral measurements may correspond to a measurement at a different depth through the skin or body of the user. In this way, a more accurate biomarker value may be calculated.

The computer-implemented method may comprise averaging the plurality of primary spectral measurements to obtain a single primary spectral measurement, which is the average of the plurality of primary spectral measurements.

In this way, a more accurate biomarker value may be calculated.

The computer-implemented method may comprise calculating a value of the biomarker using the biomarker algorithm, which takes a plurality of inputs from the respective plurality of primary spectral measurements.

In this way, a more accurate biomarker value may be calculated.

The computer-implemented method may comprise calculating a plurality of biomarker values, each biomarker value being calculated from a respective one of the plurality of primary spectral measurements. The computer-implemented method may further comprise calculating an average value of the biomarker from the plurality of biomarker values.

In this way, a more accurate biomarker value may be calculated.

The input from the primary spectral measurement may be the primary spectral measurement. The input from the primary spectral measurement may be a processed version of the primary spectral measurement. For example, the input from the primary spectral measurement may be the primary spectral measurement with a baseline correction applied to it.

The secondary measurement may be a spectral measurement.

The secondary detector may be a component of a secondary sensor. The secondary sensor may be a component of a photonic integrated circuit (PIC). The secondary sensor may further comprise a secondary light source. The secondary light source may be an infrared light source. The secondary light source may be a short-wavelength infrared (SWIR) light source. The secondary light source may be a near infrared light source. The secondary light source may be a visible light source. The secondary light source may emit light within the wavelength band 1000 nm to 2000 nm, 1280 nm to 1390 nm, or 400 nm to 2000 nm. The secondary light source may emit light at approximately 450 nm. The secondary light source may emit light in a different waveband to the primary light source. The secondary light source may emit light across the wavelength range 400 nm to 2000 nm.

The secondary light source may be an LED. The secondary light source may be a laser.

The secondary detector may be an infrared detector. The secondary detector may be a near-infrared detector. The secondary detector may be a short-wavelength infrared (SWIR) detector. The secondary detector may be a visible light detector. The secondary detector may be suitable for detecting light across the wavelength range 400 to 2400 nm. The secondary detector may be suitable for detecting a DC spectral signal. The secondary detector may be suitable for detecting an AC spectral signal.

The secondary detector may include a photodetector. The photodetector may be a silicon photodetector. The secondary detector may be a spectrometer. The secondary detector may be a spectrophotometer.

The computer-implemented method may comprise receiving a plurality of secondary spectral measurements from a respective plurality of secondary detectors. Each of the plurality of secondary photodetectors may be the same type of photodetector. Each of the plurality of secondary photodetectors may be located at a different distance from the secondary light source.

In this way, each of the plurality of secondary spectral measurements may correspond to a measurement at a different depth through the skin or body of the user. In this way, a more accurate biomarker value may be calculated.

The computer-implemented method may comprise averaging the plurality of secondary spectral measurements to obtain a single secondary spectral measurement, which is the average of the plurality of secondary spectral measurements.

The computer-implemented method may comprise calculating a value of the biomarker using the biomarker algorithm, which takes a calibration parameter from the plurality of secondary spectral measurements. The computer-implemented method may comprise calculating a value of the biomarker using the biomarker algorithm, which takes a respective plurality of calibration parameters from the plurality of secondary spectral measurements.

In this way, a more accurate biomarker value may be calculated.

The computer-implemented method may comprise calculating a plurality of biomarker values, each biomarker value being calculated from a respective one of the plurality of secondary spectral measurements. The computer-implemented method may further comprise calculating an average value of the biomarker from the plurality of biomarker values.

In this way, a more accurate biomarker value may be calculated.

The primary detector and the secondary detector may be the same detector. The plurality of primary detectors may be the same detectors as the plurality of secondary detectors. The primary detector and the secondary detector may be different detectors.

The primary sensor and the secondary sensor may be components of the same PIC. The primary sensor may be formed by the primary light sources, which may be a first subset of the light sources of the PIC, and a detector. The secondary sensor may be formed by the secondary light source, which may be a second subset of the light sources of the PIC, and the detector.

The primary sensor and the secondary sensor may be configured such that the primary light source and the secondary light source may only emit light one at a time.

In this way, the primary detector and the secondary detector may be the same detector.

The primary measurement may be made at the same time as the secondary measurement. The primary measurement and the secondary measurement may be made at different times. The primary measurement may be acquired at the same time as the secondary measurement. The primary measurement and the secondary measurement may be acquired at different times.

The primary detector may be a component of a wearable device. The secondary detector may be a component of a wearable device. The wearable device may include a watch, a bracelet, a necklace, earbuds, a glasses frame, a skin-adhesive patch, a band to be worn around the wrist, arm or leg.

The computer-implemented method may further comprise outputting the biomarker value to the user. Outputting the biomarker value to the user may comprise displaying the biomarker value on the wearable device. Outputting the biomarker value to the user may comprise displaying the biomarker value on an external device. The external device may be a mobile device such as a mobile phone.

The secondary spectral measurement may be in a different wavelength band to the primary spectral measurement.

The secondary spectral measurement may be variable with an external factor, such as a user specific characteristic, that the primary spectral measurement varies with. In this way, the secondary measurement may provide an adjustment to the input from the primary spectral measurement such that external factors, such as user-specific characteristics, are taken into account in the calculation of the biomarker value.

The secondary spectral measurement may be less variable with the biomarker value than the primary spectral measurement with the biomarker value. The secondary spectral measurement may be approximately not variable with the biomarker value. In other words, the secondary spectral measurement may be approximately constant with respect to changing biomarker values. In this way, the secondary measurement may provide an adjustment to the input from the primary spectral measurement such that external factors, such as user-specific characteristics, are taken into account in the calculation of the biomarker value.

The secondary measurement may not be a spectral measurement.

The secondary measurement may be less variable with an external factor than the primary spectral measurement is with that external factor. The secondary measurement may be approximately not variable with an external factor, such as a user specific characteristic, that the primary spectral measurement varies with. The secondary measurement may be variable with the biomarker value. In this way, the secondary measurement can provide an adjustment to the primary spectral measurement such that external factors, such as user-specific characteristics, are taken into account in the calculation of the biomarker value.

The calibration parameter may be the secondary measurement. In this way, the secondary measurement may provide an adjustment to the input from the primary spectral measurement.

The computer-implemented method may comprise receiving a plurality of secondary measurements from a respective plurality of secondary detectors. The calibration parameter may be a vector which includes the plurality of secondary measurements. In this way, data from multiple secondary detectors can be used to provide an adjustment to the primary spectral measurement.

The computer implemented method may further comprise applying a calibration model to the secondary measurement. The calibration model may take an input from the secondary measurement. The calibration model may output the calibration parameter. In this way, the secondary measurement may provide an adjustment to the input from the primary spectral measurement.

The input from the secondary spectral measurement may be the secondary spectral measurement. The input from the secondary spectral measurement may be a processed version of the secondary spectral measurement. For example, information may be extracted from the secondary spectral measurement, and this extracted information may be input into the calibration model. The information may be a user's skin scattering coefficient or a user's skin water concentration.

The calibration parameter may be a vector. In other words, the calibration parameter may include multiple calibration coefficients.

The calibration model may map the secondary measurement to an external factor affecting the biomarker measurement.

The calibration model may be a trained machine learning model.

The calibration model may be a classification model. The calibration model may be a regression model. The calibration model may be a combination of a classification model and a regression model. The calibration model may be linear. The calibration model may be non-linear. The calibration model may be a linear discriminant analysis model, a quadratic discriminant analysis model, a logistic regression model, a naïve bayes model, a decision tree model, a support vector machine model, a k-nearest neighbors model, a linear regression model, a non-linear regression model, a principal components model, a partial least squares regression model, a neural network model, a principle components analysis model, or any combination of these models.

The calibration model may be generated using training data. The calibration model being generated using training data may not limit the calibration model to being a machine learning model. The calibration model may be trained using training data.

The training data may comprise a plurality of training secondary measurements and a respective plurality of calibration parameter labels for the training secondary measurements. The calibration parameter labels may be training calibration parameters. The training calibration parameters may be calculated using respective training primary spectral measurements and respective reference values of the biomarker. Each respective training secondary measurement, training primary measurement and reference biomarker value measurement may be taken at the same time or at similar times.

The reference values of the biomarker may have been obtained via a different method to the computer-implemented method of the present invention. For example, values of oxygen saturation may have been obtained from arterial blood gas (ABG) analysis.

The training data may be obtained from a plurality of subjects. The plurality of subjects may cover a broad range of an external factor, such as an amount of melanin, which affect the primary spectral measurement. The plurality of subjects may span the space of an external factor which may affect the primary measurement. In this way, the calculation of the biomarker value may take into account that the primary spectral measurement may be dependent upon user-specific characteristics.

The training data may be obtained for a plurality of reference values of the biomarker. The plurality of reference values of the biomarker may cover a broad range of reference values of the biomarker. The plurality of reference values of the biomarker may span the space of biomarker values. In this way, the calibration model may be robust to physiological changes of the user.

The training data may be obtained for a plurality of values of a particular physiological parameter. For example, the training data may be obtained for a plurality of temperatures of a user, for a plurality of metabolite concentrations of a user, for a plurality of hydration states of the user, or for a plurality of oxygen saturations of the user. The plurality of values of the particular physiological parameter may cover a broad range of values. The plurality of values of the particular physiological parameter may span the space for the particular physiological parameter. In this way, the calibration model may be robust to physiological changes of the user.

The training data may be obtained from a plurality of primary detectors. The training data may be obtained from a plurality of primary sensors. The training data may be obtained from a plurality of secondary detectors. The training data may be obtained from a plurality of secondary sensors. In this way, the calibration model may be robust to sensor changes.

The training data may be obtained for a plurality of activity levels of a subject. The training data may be obtained for a plurality of motion levels of a subject. For example, training data may be obtained when the user is at rest and when the user is exercising. In this way, the calibration model may be robust to changes in the activity level and/or motion level of the user.

The calibration model may be validated using similar datasets to those used for the training. The calibration model may be validated using datasets obtained from new subjects to those used for the training. The calibration model may be validated using datasets obtained from new detectors to those used for the training. The new detectors may be components of new sensors. In validation, the final parameters of the calibration model may be chosen and may remain fixed for testing.

The computer-implemented method may further comprise storing the primary spectral measurement. The computer-implemented method may further comprise storing the secondary measurement. The training data may include historical user-specific data. The historical user-specific data may include stored primary spectral measurements and stored secondary measurements.

In this way, the biomarker values calculated may be more accurate for the specific user.

The biomarker algorithm may be a trained machine learning model.

The biomarker algorithm may be a classification model. The biomarker algorithm may be a regression model. The biomarker algorithm may be a combination of a classification model and a regression model. The biomarker algorithm may be non-linear. The biomarker algorithm may be a linear discriminant analysis model, a quadratic discriminant analysis model, a logistic regression model, a naïve bayes model, a decision tree model, a support vector machine model, a k-nearest neighbors model, a linear regression model, a non-linear regression model, a principal components model, a partial least squares regression model, a neural network model, a principle components analysis model, or any combination of these models.

The biomarker algorithm may be generated using training data. The biomarker algorithm being generated using training data may not limit the calibration model to being a machine learning model. The biomarker algorithm may be trained using training data.

The training data may comprise a plurality of training primary spectral measurements, a respective plurality of training secondary measurement datasets, and a respective plurality of reference biomarker value labels. Each training secondary measurement dataset may include a plurality of training secondary measurements each received from a different secondary detector. Each respective training primary measurement, training secondary measurement dataset and reference biomarker value may be measured at the same time or at similar times.

The reference values of the biomarker may have been obtained via a different method to the computer-implemented method of the present invention.

The training data may be obtained from a plurality of subjects. The plurality of subjects may cover a broad range of an external factor, such as an amount of melanin, which affect the primary spectral measurement. The plurality of subjects may span the space of an external factor which may affect the primary measurement. In this way, the calculation of the biomarker value may take into account that the primary spectral measurement may be dependent upon user-specific characteristics.

The training data may be obtained for a plurality of reference values of the biomarker. The plurality of reference values of the biomarker may cover a broad range of reference values of the biomarker. The plurality of reference values of the biomarker may span the space of biomarker values. In this way, the biomarker algorithm may be robust to physiological changes of the user.

The training data may be obtained for a plurality of values of a particular physiological parameter. For example, the training data may be obtained for a plurality of temperatures of a user, for a plurality of metabolite concentrations of a user, for a plurality of hydration states of the user, or for a plurality of oxygen saturations of the user. The plurality of values of the particular physiological parameter may cover a broad range of values. The plurality of values of the particular physiological parameter may span the space for the particular physiological parameter. In this way, the biomarker algorithm may be robust to physiological changes of the user.

The training data may be obtained from a plurality of primary detectors. The training data may be obtained from a plurality of primary sensors. The training data may be obtained from a plurality of secondary detectors. The training data may be obtained from a plurality of secondary sensors. In this way, the biomarker algorithm may be robust to sensor changes.

The training data may be obtained for a plurality of activity levels of a subject. The training data may be obtained for a plurality of motion levels of a subject. For example, training data may be obtained when the user is at rest and when the user is exercising. In this way, the biomarker algorithm may be robust to changes in the activity level and/or motion level of the user.

The biomarker algorithm may be validated using similar datasets to those used for the training. The biomarker algorithm may be validated using datasets obtained from new subjects to those used for the training. The biomarker algorithm may be validated using datasets obtained from new detectors to those used for the training. The new detectors may be components of new sensors. In validation, the final parameters of the biomarker algorithm may be chosen and may remain fixed for testing.

The computer-implemented method may further comprise storing the primary spectral measurement. The computer-implemented method may further comprise storing the secondary measurement. The training data may include historical user-specific data. The historical user-specific data may include stored primary spectral measurements and stored secondary measurements.

In this way, the biomarker values calculated may be more accurate for the specific user.

The primary spectral measurement may include measurements suitable for calculating a PPG value of oxygen saturation. In this case, the primary spectral measurement may be referred to as a PPG measurement. The primary spectral measurement may include a measurement of red waveband spectral data and a measurement of infrared waveband spectral data. The primary spectral measurement may include an AC spectral measurement. In this case, the primary spectral measurement may be referred to as a PPG measurement. The primary spectral measurement may include a DC spectral measurement. A DC spectral measurement may measure a bulk property of tissue. A bulk property of tissue may include, for example, skin pigmentation, amount of melanin, and temperature. DC signals may be measured across the full optical spectrum. In one or more embodiments, that may be 400-2400 nm. The primary spectral measurement may include an AC measurement of red waveband spectral data and an AC measurement of infrared waveband spectral data. The primary spectral measurement may include a DC measurement of red waveband spectral data and a DC measurement of infrared waveband spectral data.

The input from the primary spectral measurement may be a modulation ratio at a first waveband divided by a modulation ratio at a second waveband. The first waveband may be a red wavelength waveband. The second waveband may be an infrared wavelength waveband. A modulation ratio may be a ratio of an AC measurement to a DC measurement. The input from the primary spectral measurement may be $R=(AC_{RED}/DC_{RED})/(AC_{IR}/DC_{IR})$, where R is the input from the primary spectral measurement, $AC_{RED}$ is the AC measurement at a red waveband, $DC_{RED}$ is the DC measurement at a red waveband, $AC_{IR}$ is the AC measurement at an infrared waveband, and $DC_{IR}$ is the DC measurement at an infrared waveband.

The biomarker may be oxyhemoglobin and/or de-oxyhemoglobin. The biomarker value may be oxygen saturation. The biomarker value may be functional oxygen saturation (SpO2). Functional saturation may be the ratio of the amount of oxy-hemoglobin to the sum of the amount of deoxy-hemoglobin and the amount of oxy-hemoglobin. The biomarker value may be fractional oxygen saturation. Fractional saturation may be the ratio of the amount of oxy-hemoglobin to the sum of the amount of deoxy-hemoglobin, the amount of oxy-hemoglobin, the amount of carboxy-hemoglobin and the amount of met-hemoglobin. The biomarker algorithm may calculate functional oxygen saturation as follows: $SpO2=b_0+b_1R+b_2R^2$, where $\underline{b}=(b_0, b_1, b_2)$ is the calibration parameter, and where R is input from the primary spectral measurement.

In this way, a more accurate oxygen saturation value may be calculated.

The secondary measurement may be a measurement of infrared spectral data. The secondary measurement may be a measurement of short wavelength infrared (SWIR) spectral data. The secondary measurement may be a measurement of visible wavelength spectral data. The secondary measurement may be a measurement of spectral data within the wavelength band 1000 nm to 2000 nm. The secondary measurement may be a measurement of spectral data within the wavelength band 1280 nm to 1390 nm. In this way, a more accurate biomarker value may be calculated, by taking into account effects of skin pigmentation, amount of melanin, skin thickness, BMI, and/or amount of other hemoglobin species such as carboxy-hemoglobin and met-hemoglobin. In some embodiments the effects may be accounted for using a specific wavelength range. In some embodiments, the effects may be accounted for using a specific component of the detector measurement, which may be the static (DC) or the pulsatile (AC/DC) component of the detector measurement. In some embodiments, the effects of skin pigmentation and amount of melanin may be accounted for using a DC component of the detector measurement. In some embodiments, the effects of skin pigmentation and amount of melanin may be strongest in the wavelength range 500 nm to 1000 nm. In some embodiments, the effects of skin pigmentation and amount of melanin may be accounted for using light within the wavelength range 500 nm to 1000 nm. In some embodiments, the effects of skin pigmentation and amount of melanin may be accounted for using light up to 1400 nm. In some embodiments, the effects of carboxy-hemoglobin and met-hemoglobin may be accounted for using the pulsatile component of the detector measurement. In some embodiments, the effect of carboxy-hemoglobin may be accounted for using light within the wavelength range 500 nm to 900 nm. In some embodiments, the effect of met-hemoglobin may be accounted for using light within the wavelength range 500 nm to 1200 nm. The secondary measurement may be a measurement of spectral data at approximately 450 nm. In this way, a more accurate biomarker value may be calculated, by taking into account effects of amount of bilirubin. The secondary measurement may be a measurement of spectral data in the wavelength band 400 nm to 2000 nm.

The primary spectral measurement may be a measurement of short wavelength infrared spectral data. The primary spectral measurement may be a measurement within the waveband 1280 nm to 1644 nm, 1290 nm to 1654 nm, 1290 nm to 2382 nm, or 1000 nm to 2500 nm.

The biomarker may be body temperature. The biomarker may be core body temperature.

The secondary measurement may be a direct or an indirect temperature measurement. The secondary measurement may be a direct or an indirect core body temperature measurement. The secondary measurement may be a skin surface temperature measurement. The secondary measurement may be an ambient temperature measurement. The secondary detector may be a thermometer. The secondary detector may be a thermistor. The secondary measurement may be a heart rate measurement. The measurement may be made using a photoplethysmogram (PPG). The secondary detector may be a PPG detector. The secondary sensor may be a PPG sensor. The secondary sensor may include a secondary light source which emits light in the green light waveband. The secondary light source may emit light at approximately 527 nm. The secondary measurement may be a humidity measurement. The secondary detector may be a hygrometer. The secondary measurement may be a measurement of mass transfer conditions. Mass transfer conditions may include a movement of the user, a blood flow, or a thermal conductivity of a material. The secondary detector may be an accelerometer such as an inertial measurement unit (IMU). The secondary detector may be a gyroscope. The secondary detector may be a speckle-photoplethysmograph (SPG) sensor. In this way, a more accurate body temperature value may be calculated, by taking into account other measurements of body temperature.

The primary spectral measurement may be a measurement of spectral data within the wavelength band 1500 nm to 1900 nm. The primary spectral measurement may be a measurement of spectral data within the wavelength band 1650 nm to 1780 nm. In this way, a biomarker value for glucose may be calculated. The primary spectral measurement may be a measurement of spectral data within the wavelength band 1900 nm to 2500 nm. The primary spectral measurement may be a measurement of spectral data within the wavelength band 2050 nm to 2380 nm. In this way, a biomarker value for glucose may be calculated.

The biomarker may be a metabolite. The biomarker may be water, collagen, temperature, ethanol, lactate, glucose or urea.

In a second aspect, embodiments of the invention provide a computer program which when run causes a processor to carry out a method according to the first aspect of the invention.

In a third aspect, embodiments of the invention provide a device comprising a processor, the processor configured to carry out a method according to the first aspect of the invention.

In a fourth aspect, embodiments of the invention provide a device comprising a primary sensor comprising a primary detector and a secondary sensor comprising a secondary detector, such that the device is suitable for measuring a primary spectral measurement and a secondary spectral measurement. The primary sensor and the secondary sensor may be those according to the first aspect of the invention. The primary spectral measurement and the secondary measurement may be those according to the first aspect of the invention. For example, the device may comprise a SWIR sensor and a PPG sensor. The device may comprise a SWIR sensor and a thermometer, a thermistor, a PPG sensor, or a hygrometer. The spectrum of each laser may have a significantly narrower waveband than the spectrum of an LED centered on the same wavelength as the spectrum of the laser.

In a fifth aspect, embodiments of the invention provide a device which is according to both the third aspect and the fourth aspect of the invention.

BRIEF DESCRIPTION OF THE DRAWINGS

These and other features and advantages of the present invention will be appreciated and understood with reference to the specification, claims, and appended drawings wherein:

DETAILED DESCRIPTION

The detailed description set forth below in connection with the appended drawings is intended as a description of exemplary embodiments of a computer-implemented method provided in accordance with the present invention and is not intended to represent the only forms in which the present invention may be constructed or utilized. The description sets forth the features of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like elements or features.

Embodiments of a first aspect of the invention provide a computer-implemented method to improve the accuracy of a calculation of a biomarker value from a spectral measurement, the computer-implemented method comprising receiving a primary spectral measurement from a primary detector, receiving a secondary measurement from a secondary detector, and calculating a value of the biomarker using a biomarker algorithm, which takes an input from the primary spectral measurement and a calibration parameter from the secondary measurement. Detailed embodiments of the present invention will now be described.

Functional Oxygen Saturation (SpO2)

Figure 1:
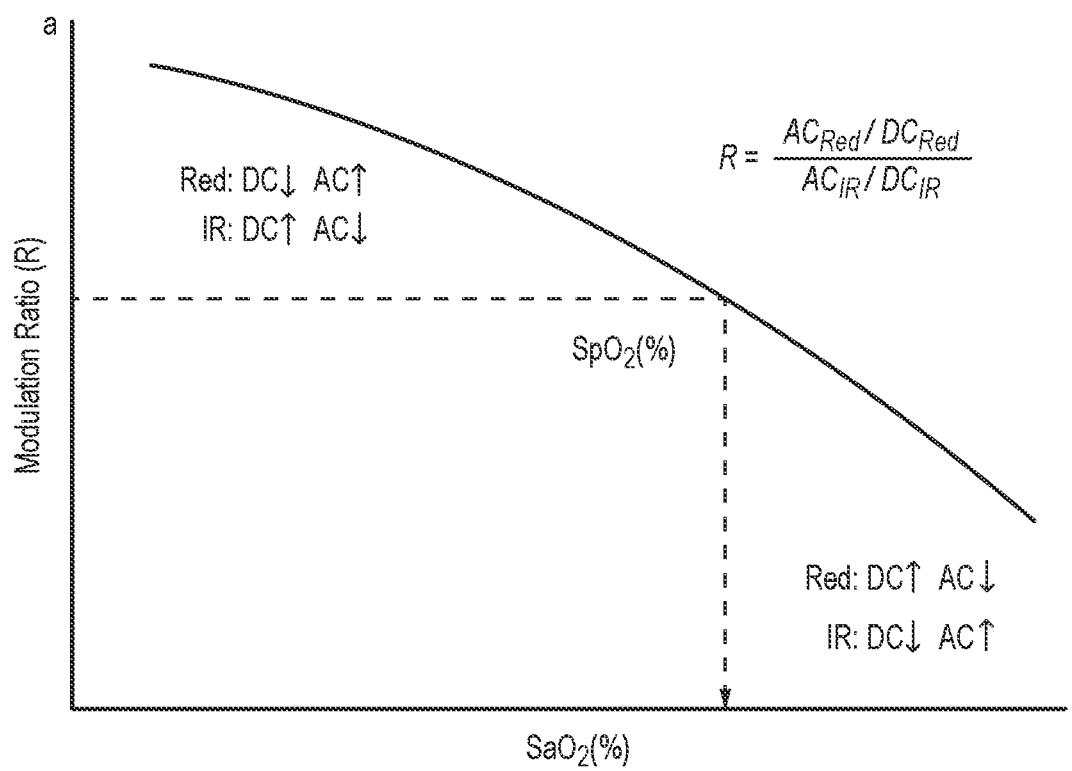
FIG. 1 is a plot of SaO2(%) against modulation ratio (R).

In the art, a pulse oximeter can be used to measure functional oxygen saturation (SpO2). Functional oxygen saturation estimation algorithms use the ratio of an AC measurement to a DC measurement (a modulation ratio) at two wavebands (red and IR) to estimate functional oxygen saturation by: $SpO2 = b_0 + b_1 R + b_2 R^2$ wherein $b_0$, $b_1$, $b_2$ are calibration coefficients, $R = (AC_{RED}/DC_{RED})/(AC_{IR}/DC_{IR})$, where $AC_{RED}$ is the AC measurement at a red waveband, $DC_{RED}$ is the DC measurement at a red waveband, $AC_{IR}$ is the AC measurement at an infrared waveband, and $DC_{IR}$ is the DC measurement at an infrared waveband. FIG. 1 shows the variation of the modulation ratio (R) with oxygen saturation (SaO2).

In the art, the calibration coefficients may be determined as part of the design and manufacture of the pulse oximeter. Each pulse oximeter may have its own set of calibration coefficients due to manufacturing variability. However, the calibration coefficients may depend upon a user-specific characteristic. Therefore, user-specific characteristics may affect the accuracy of the functional oxygen saturation value. For example, the accuracy of the functional oxygen saturation value may be affected by skin pigmentation at low oxygen saturation values.

A first embodiment of a first aspect of the invention provides a computer-implemented method to improve the accuracy of a calculation of functional oxygen saturation.

The computer-implemented method comprises receiving a primary spectral measurement, which includes an AC spectral measurement at a red waveband ($AC_{RED}$), a DC spectral measurement at a red waveband ($DC_{RED}$), an AC spectral measurement at an infrared waveband ($AC_{IR}$) and a DC spectral measurement at an infrared waveband ($DC_{IR}$). The primary spectral measurement is received from a primary detector which is a PPG detector.

The computer-implemented method further comprises receiving a secondary spectral measurement, which is a SWIR measurement. The secondary spectral measurement is received from a SWIR detector. The SWIR measurement is a static measurement, and therefore measures a bulk absorption. The SWIR measurement may be affected by skin pigmentation, amount of melanin, skin thickness, amount of other hemoglobin species such as carboxy-hemoglobin and met-hemoglobin, and/or amount of bilirubin.

In alternative embodiments, the secondary spectral measurement may be in a wavelength band other than the SWIR wavelength band.

The computer-implemented method further comprises calculating a value for functional oxygen saturation using a biomarker algorithm. The biomarker algorithm takes an input from the primary spectral measurement and a calibration parameter from the secondary measurement.

The input from the primary spectral measurement is a modulation ratio R, where $R=(AC_{RED}/DC_{RED})/(AC_{IR}/DC_{IR})$. In alternative embodiments, the modulation ratio R may be defined differently. For example, the primary spectral measurement may include AC and DC spectral measurements at a waveband other than the red and infrared wavebands, and the modulation ratio R may be a modulation ratio of these spectral measurements.

The calibration parameter from the secondary measurement is a vector $\underline{b}$ of calibration coefficients $b_0$, $b_1$, $b_2$. The calibration parameter $\underline{b}$ is output by a calibration model f applied to the secondary spectral measurement. The calibration model f estimates $\underline{b}$ for subject i as $\underline{b}_i = f(x_i)$, where $\underline{b}_i$ is the calibration parameter for subject i, and where $x_i$ is the secondary spectral measurement for subject i.

Alternatively, the calibration model f could be applied to information extracted from the secondary spectral measurement, which may be the subject's skin scattering coefficient or skin water concentration, for example.

The calibration parameter $\underline{b}$ output by the calibration model f is input into the biomarker algorithm.

The biomarker algorithm calculates functional oxygen saturation as follows: $SpO2 = b_0 + b_1 R + b_2 R^2$, where $\underline{b} = (b_0, b_1, b_2)$ is the calibration parameter, and where R is the input from the primary spectral measurement.

In alternative embodiments, an alternative biomarker algorithm may be used. For example, as discussed above, the modulation ratio R may be differently defined. The biomarker algorithm may take into account a plurality of modulation ratios. Taking into account more modulation ratios may result in a more accurate biomarker value calculation. Taking into account modulation ratios with a broader range of wavelengths may increase the accuracy of the oxygen saturation calculation.

Figure 2:
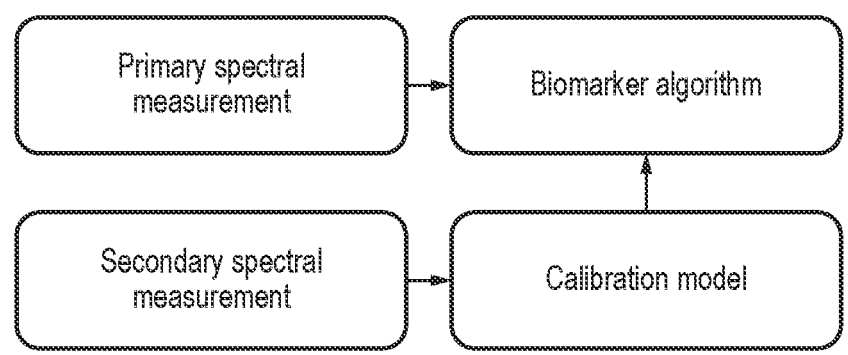
FIG. 2 is a diagram showing a biomarker calculation method according to an embodiment of the present invention.

FIG. 2 is a diagram showing the biomarker calculation method according to the present embodiment. FIG. 2 shows that the biomarker algorithm takes an input from the primary spectral measurement and an input from the output of the calibration model. The output of the calibration model is the calibration parameter. FIG. 2 further shows that the calibration model takes an input from the secondary spectral measurement.

In this way, the calibration parameter obtained from the secondary measurement provides an adjustment to the primary spectral measurement such that external factors, such as user-specific characteristics, are taken into account in the calculation of the functional oxygen saturation.

The calibration model is a model which has been generated using training data.

The training data comprises a plurality of training secondary measurements, which are SWIR measurements, and a respective plurality of calibration parameter labels for the training secondary measurements. The calibration parameter labels are training calibration parameters which are calculated using respective training primary spectral measurements, which are training $AC_{RED}$, $DC_{RED}$, $AC_{IR}$ and $DC_{IR}$ measurements and which are used to calculate R, and respective reference oxygen saturation values which are oxygen saturation measurements (for example arterial oxygen saturation (SaO2) measurements) measured using an accepted reference method such as the clinical blood gas analyzer method. The training calibration parameters are calculated by rearranging the above SpO2 equation.

For each subject, the measurements of the training primary spectral measurements, training secondary measurements, and reference values are taken as the subject's oxygen saturation (for example arterial oxygen saturation) is varied. Each respective training secondary measurement, training primary measurement and reference oxygen saturation value measurement are taken at the same time or at similar times.

The training data spans spaces which affect the calculated oxygen saturation. For example, the training data is obtained from plurality of subjects which together span the space of an external factor, such as skin colour, which affects the primary spectral measurement. The training data is also obtained for a broad range of reference oxygen saturation values, which span the space of oxygen saturation values.

The calibration model is validated using similar datasets to those used for the training. The calibration model may be validated using datasets obtained from new subjects to those used for the training. The calibration model may be validated using datasets obtained from different sensors to those used for the training. In validation, the final parameters of the calibration model are chosen and remain fixed for testing.

According to the present embodiment, the computer-implemented method may increase the accuracy of a functional oxygen saturation calculation.

Core Body Temperature ($T_c$)

Core body temperature (Tc) can be estimated non-invasively using SWIR spectroscopy. This technique is sensitive to external factors. For example, this technique is sensitive to the temperature of water and other skin components.

A second embodiment of a first aspect of the invention provides a computer-implemented method to improve the accuracy of a calculation of a core body temperature value.

The computer-implemented method comprises receiving a primary spectral measurement, which is a SWIR measurement, from a primary detector, which is a SWIR detector.

The computer-implemented method further comprises receiving one or more secondary measurements from a respective one or more secondary detectors. The one or more secondary measurements are additional measurements of body temperature, which may be direct or indirect measurements of body temperature. For example, a secondary measurement may be a skin surface temperature measurement taken with a thermometer, and a secondary measurement may be a heart rate measurement at approximately 527 nm taken with a PPG sensor. Some or all of the secondary measurements are approximately constant with an external factor that the primary spectral measurement varies with, such as skin thickness and skin pigmentation.

The computer-implemented method further comprises calculating a value of the core body temperature using a biomarker algorithm, which takes an input from the primary spectral measurement and an input from a vector of the one or more secondary measurements.

The biomarker algorithm f calculates a value of the core body temperature ($T_c$) as $T_c = f(x, y)$, where x is the primary spectral measurement and where y is a vector which includes the one or more secondary measurements. The vector of secondary measurements acts as a calibration parameter for the primary spectral measurement.

Figure 3:
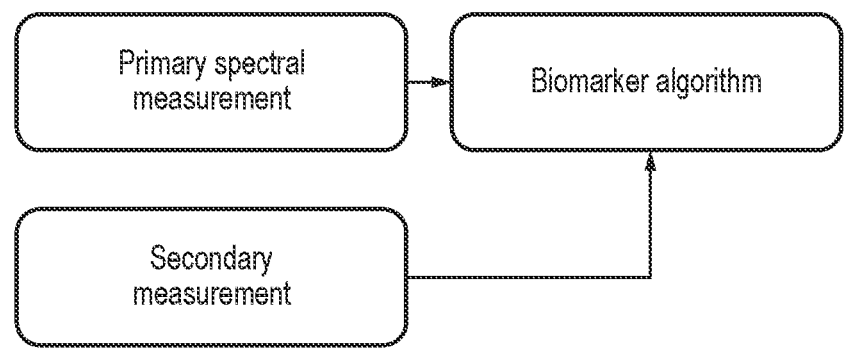
FIG. 3 is a diagram showing a biomarker calculation method according to an embodiment of the present invention.

FIG. 3 is a diagram showing the biomarker calculation method according to the present embodiment. FIG. 3 shows that the biomarker algorithm takes an input from the primary spectral measurement and an input from the secondary measurement.

In this way, data from one or more secondary detectors can be used to provide an adjustment to the primary spectral measurement such that the effect of external factors on the core body temperature calculation is reduced.

The biomarker algorithm is a trained machine learning model, trained using training data.

The training data comprises a plurality of training primary spectral measurements, which are SWIR measurements, a respective plurality of training secondary measurement datasets, and a respective plurality of reference temperature labels which are reference temperature measurements. Each training secondary measurement dataset includes one or more training secondary measurements each of the one or more training secondary measurements received from a different secondary detector.

The reference temperature measurements are made via an accepted reference method.

For each subject from which the training data is taken, the measurements of the training primary spectral measurements, training secondary measurements, and reference values are taken as the subject's core body temperature is varied.

Each respective training primary spectral measurement, training secondary measurement and reference temperature measurement are measured at the same time or at similar times.

The training data spans the spaces of parameters which may affect the calculated temperature. For example, the training data is obtained from plurality of subjects which together span the space of an external factor, such as skin colour, which affect the primary spectral measurement. The training data is obtained for a broad range of reference temperatures, which span the space of body temperature.

The biomarker algorithm is validated using similar datasets to those used for the training. The biomarker algorithm may be validated using datasets obtained from new subjects to those used for the training. The biomarker algorithm may be validated using datasets obtained from different sensors to those used for the training. In validation, the final parameters of the biomarker algorithm are chosen and remain fixed for testing.

According to the present embodiment, the computer-implemented method may increase the accuracy of a core body temperature calculation.

General Biomarker Measurement

Biomarkers are known to have informative spectral regions for their detection, classification and quantification. For example, SpO2 measurements may be taken using red and IR LEDs centered at 660 nm and 940 nm, respectively. Glucose informative spectral regions are 1650 nm to 1780 nm and 2050 nm to 2380 nm.

Different subjects may have slightly different spectral signatures for a given biomarker. This is because the optical properties and layer thicknesses of the skin and subcutaneous tissue affect the light pathlength traveled through the tissue volumes containing the biomarker, and optical properties and layer thicknesses vary by subject. For example, two subjects with different levels of melanin content will have different wavelength-dependent signatures of oxyhemoglobin and deoxyhemoglobin. As another example, two subjects with different dermal thicknesses will have different wavelength-dependent signatures of glucose.

A third embodiment of a first aspect of the invention provides a computer-implemented method to improve the accuracy of a calculation of a biomarker value from a spectral measurement. The biomarker may be a metabolite. The biomarker value may be a metabolite concentration. The biomarker may be water, collagen, temperature, ethanol, lactate, glucose or urea. The biomarker value may be glucose concentration.

The computer-implemented method comprises receiving a primary spectral measurement. For a biomarker value of glucose concentration, the primary spectral measurement may be a measurement of spectral data in the wavelength band 1650 nm to 1780 nm, or 2050 nm to 2380 nm. The primary spectral measurement is received from a primary detector, which is an infrared detector for a biomarker value of glucose concentration.

The computer implemented method further comprises receiving a secondary spectral measurement from a secondary detector. The secondary spectral measurement is in a different wavelength band to the primary spectral measurement, such that the secondary spectral measurement varies with an external factor, such as a user specific characteristic, that the primary spectral measurement varies with, but is approximately constant with respect to changing biomarker values. For a biomarker value of glucose concentration, the secondary spectral measurement is therefore approximately constant with respect to changing biomarker values.

In this way, the secondary spectral measurement can provide an adjustment to the primary spectral measurement such that external factors, such as user-specific characteristics, are taken into account in the calculation of the biomarker value.

For example, if the secondary spectral measurement does not contain direct information about light absorption by a biomarker but does contain information about a subject's optical properties or skin layer thicknesses, then the secondary spectral measurement allows calibration of the calculation of the biomarker value. The calculation of the biomarker value takes into account the information about the subject's optical properties or skin layer thickness. For example, if the secondary spectral measurement contains information about melanin content, it may help correct for melanin dependent spectral signature differences in oxy and deoxy haemoglobin when calculating oxygen saturation. As another example, if secondary spectral measurement contains information about dermal thickness, it may help correct for dermal thickness dependent spectral signature differences in glucose when calculating glucose concentration.

Figure 4:
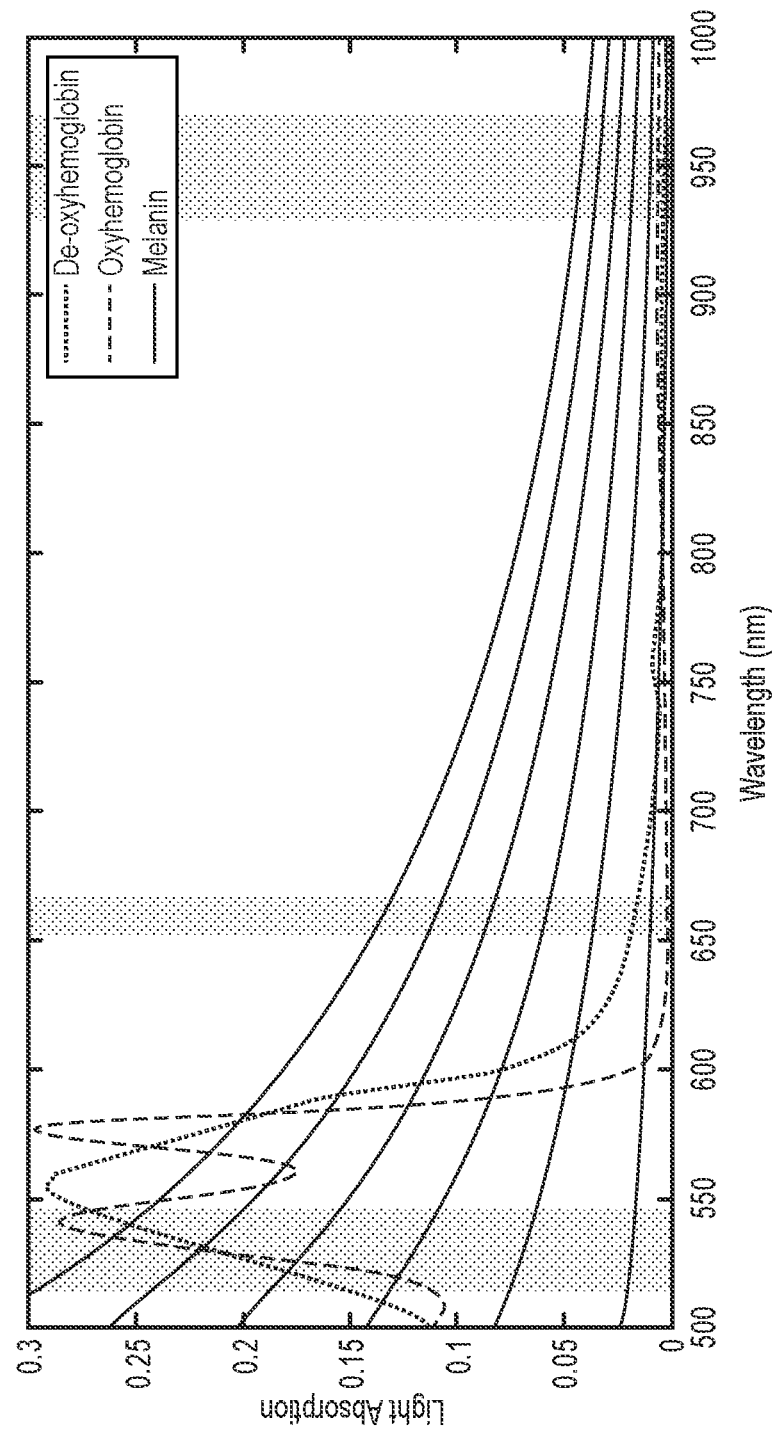
FIG. 4 is a plot of light absorption against wavelength for de-oxyhemoglobin, oxyhemoglobin and melanin.

FIG. 4 shows a plot of light absorption against wavelength for de-oxyhemoglobin, oxyhemoglobin and melanin.

Figure 5:
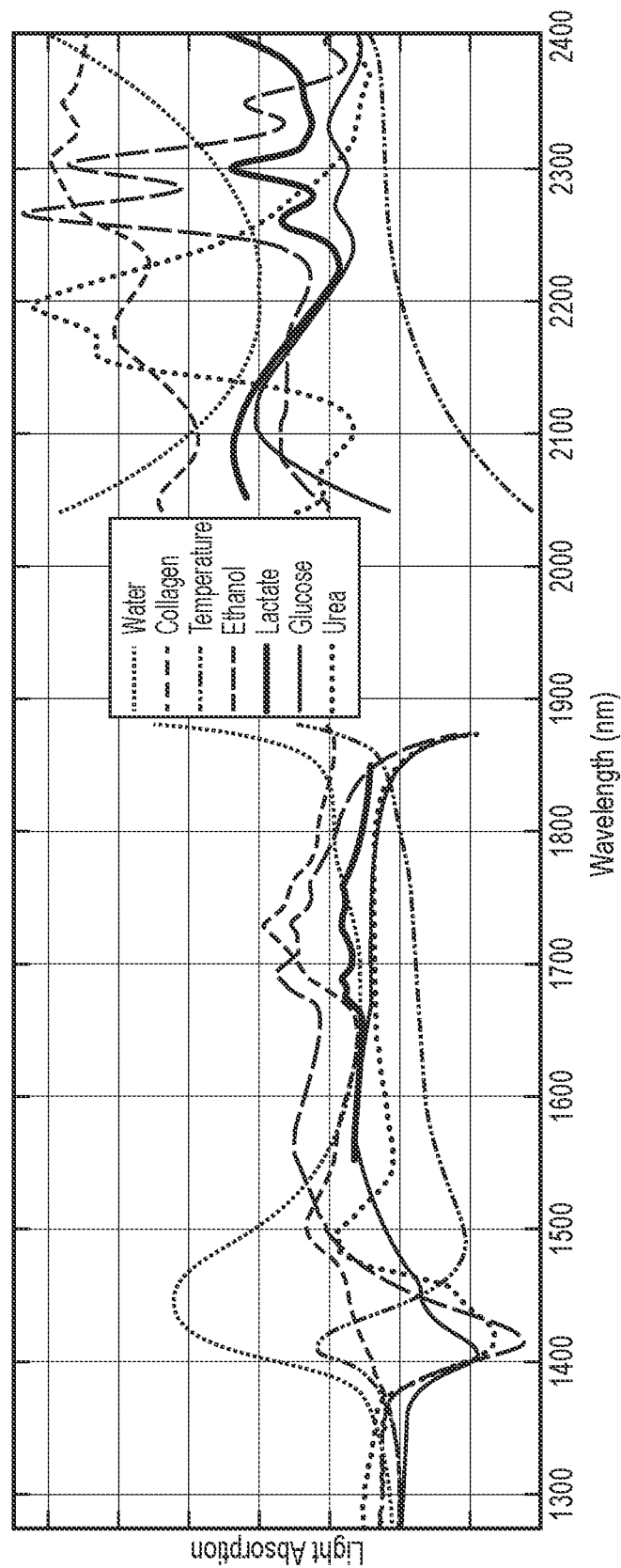
FIG. 5 is a plot of light absorption against wavelength for water, collagen, temperature, ethanol, lactate, glucose and urea.

FIG. 5 shows a plot of light absorption against wavelength for water, collagen, temperature, ethanol, lactate, glucose and urea.

The computer-implemented method further comprises calculating the biomarker value using a biomarker algorithm.

Figure 6A:
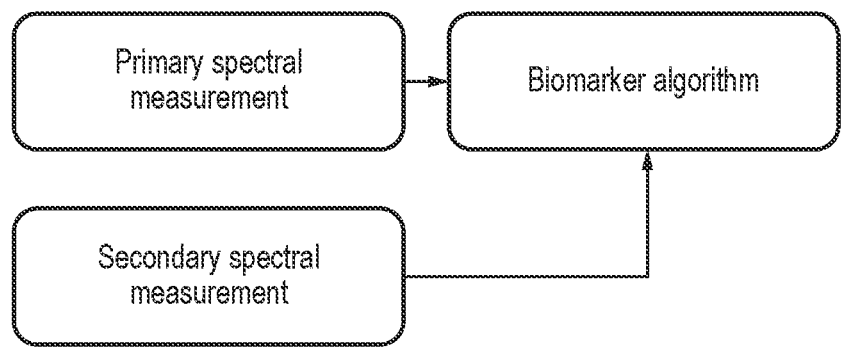
FIG. 6A is a diagram showing a biomarker calculation method according to an embodiment of the present invention.

In some embodiments, the biomarker algorithm takes an input from the primary spectral measurement and an input from the secondary spectral measurement. FIG. 6A is a diagram showing the biomarker calculation method according to this case. FIG. 6A shows that the biomarker algorithm takes an input from the primary spectral measurement and an input from the secondary spectral measurement.

In this case, the biomarker algorithm is a trained machine learning model, trained using training data.

The training data comprises a plurality of training primary spectral measurements, a respective plurality of training secondary spectral measurements, and a respective plurality of reference biomarker value labels which are reference biomarker values.

The reference biomarker values are measured via an accepted reference method.

For each subject from which the training data is taken, the measurements of the training primary spectral measurements, training secondary spectral measurements, and reference values are taken as the subject's biomarker value is varied. For example, if the biomarker value is glucose concentration, the subject's glucose concentration is varied.

Each respective training primary spectral measurement, training secondary spectral measurement and reference temperature measurement are measured at the same time or at similar times.

The training data spans the spaces of parameters which may affect the calculated biomarker value. For example, the training data is obtained from plurality of subjects which together span the space of an external factor, such as skin colour, which affect the primary spectral measurement. The training data is also obtained for a broad range of biomarker values, which span the space of the biomarker values.

The biomarker algorithm is validated using similar datasets to those used for the training. The biomarker algorithm may be validated using datasets obtained from new subjects to those used for the training. The biomarker algorithm may be validated using datasets obtained from different sensors to those used for the training. In validation, the final parameters of the biomarker algorithm are chosen and remain fixed for testing.

In other embodiments, the computer implemented method comprises applying a calibration model to the secondary spectral measurement. The calibration model takes an input from the secondary spectral measurement, and the calibration model outputs a calibration parameter. The computer-implemented method further comprises calculating the biomarker value using a biomarker algorithm which takes an input from the primary spectral measurement and an input from the calibration parameter.

The input from the secondary spectral measurement into the calibration model may be the raw secondary spectral measurement or may be a processed version of the raw secondary spectral measurement. For example, information may be extracted from the secondary spectral measurement, and this extracted information may be input into the calibration model. The information may be a user's skin scattering coefficient or a user's skin water concentration.

Figure 6B:
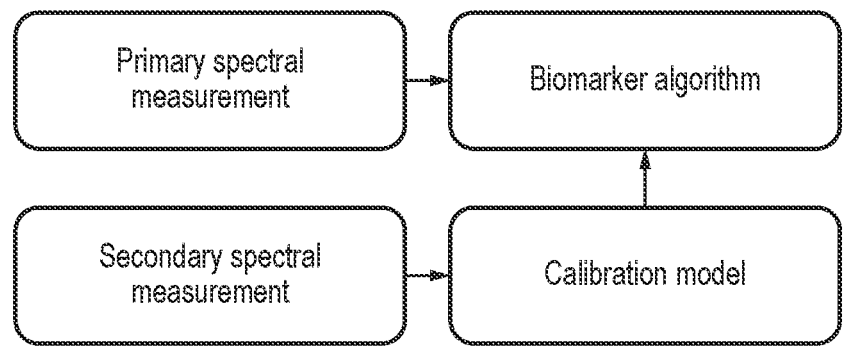
FIG. 6B is a diagram showing a biomarker calculation method according to an embodiment of the present invention.

FIG. 6B is a diagram showing the biomarker calculation method according to this case. FIG. 6B shows that the biomarker algorithm takes an input from the primary spectral measurement and an input from the output of the calibration model. The output of the calibration model is the calibration parameter. FIG. 6B further shows that the calibration model takes an input from the secondary spectral measurement.

In this case, the calibration model may be a trained machine learning model, which has been trained using training data.

The training data comprises a plurality of training secondary measurements, and a respective plurality of calibration parameter labels for the training secondary measurements. The calibration parameter labels are training calibration parameters which are calculated using respective training primary spectral measurements, and respective reference biomarker values. The reference biomarker values are measured using an accepted reference method.

For each subject, the measurements of the training primary spectral measurements, training secondary measurements, and reference values are taken as the subject's biomarker value is varied. Each respective training secondary measurement, training primary measurement and reference biomarker value measurement are taken at the same time or at similar times.

The training data spans the spaces of parameters which may affect the calculated biomarker value. For example, the training data is obtained from plurality of subjects which together span the space of an external factor, such as skin colour, which affect the primary spectral measurement. The training data is also obtained for a broad range of reference biomarker values which span the space of biomarker values.

The calibration model is validated using similar datasets to those used for the training. The calibration model may be validated using datasets obtained from new subjects to those used for the training. The calibration model may be validated using datasets obtained from different sensors to those used for the training. In validation, the final parameters of the calibration model are chosen and remain fixed for testing.

In this way, the computer-implemented method may increase the accuracy of biomarker value calculations which use spectral measurements that are variable with a factor external to the biomarker.

Figure 7:
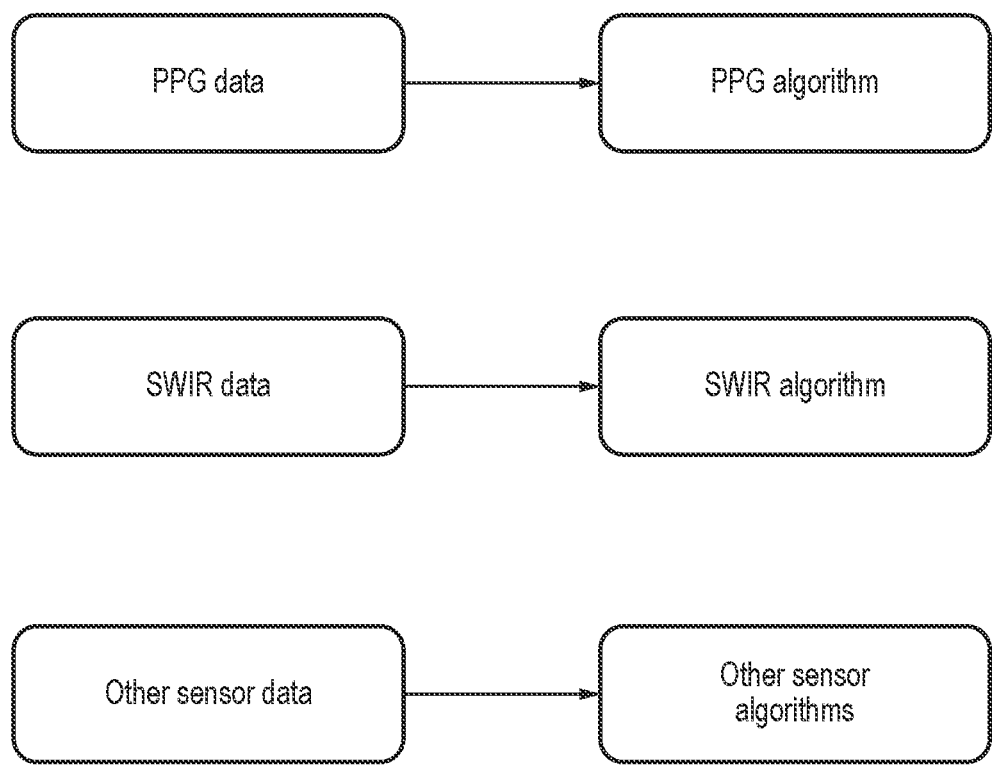
FIG. 7 is a diagram showing biomarker calculation methods according to the prior art.

FIG. 7 is a diagram showing biomarker calculation methods according to the prior art. FIG. 7 shows that a given biomarker algorithm may take primary measurements only as inputs into the biomarker algorithm. For example, the PPG algorithm to analyze PPG measurements takes only PPG measurements as an input, the SWIR algorithm to analyze SWIR measurements, takes only SWIR measurements as an input, and other detector algorithms to analyze other detector measurements, takes only the other detector measurements as an input.

Figure 8:
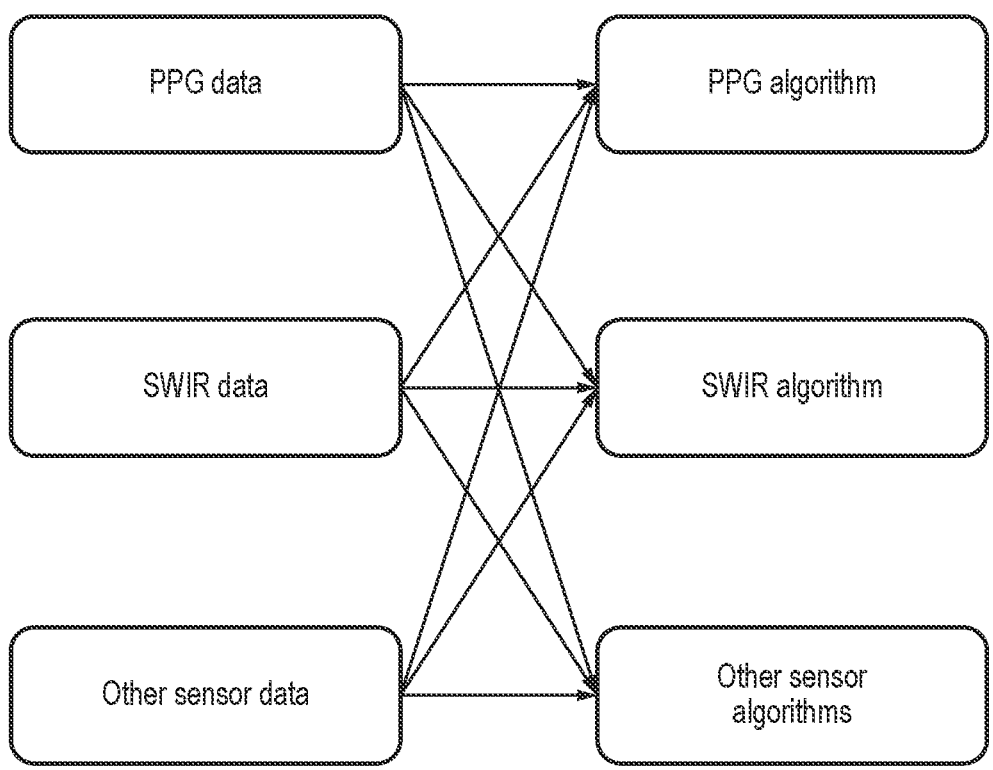
FIG. 8 is a diagram showing biomarker calculation methods according to embodiments of the present invention.
Figure 9:
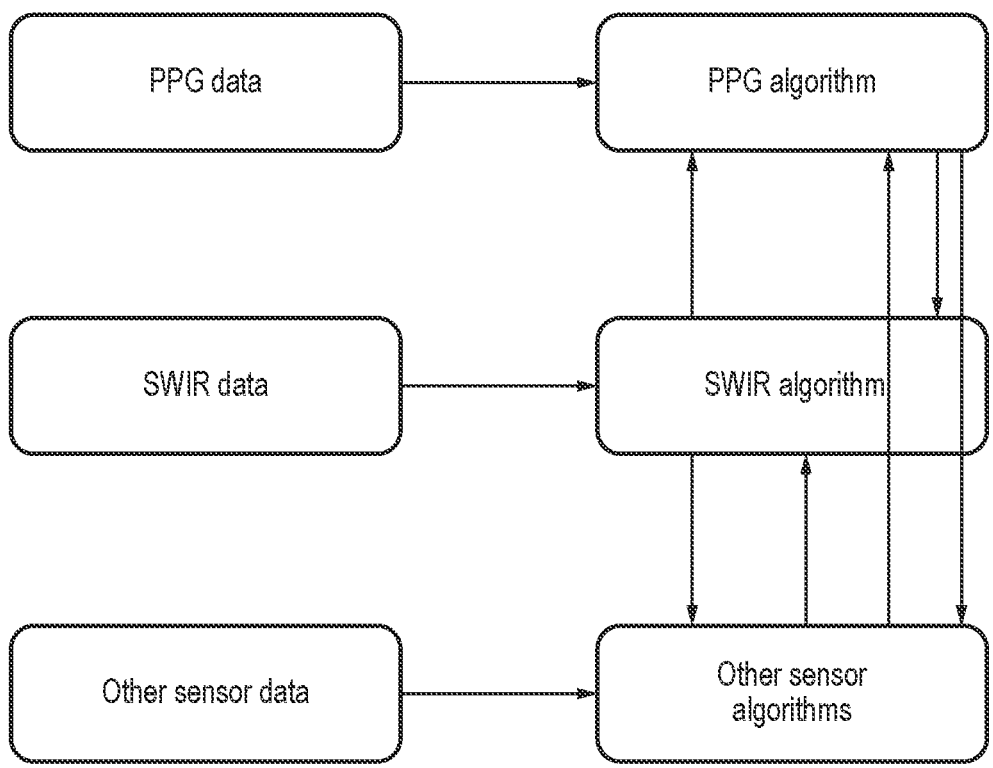
FIG. 9 is a diagram showing biomarker calculation methods according to embodiments of the present invention.

In contrast, FIGS. 8 and 9 show biomarker calculation methods according to embodiments of the present invention.

FIG. 8 shows that inputs from both primary and secondary measurements may be input into a biomarker algorithm. For example, a PPG algorithm to analyze PPG measurements may take inputs from PPG measurements, SWIR measurements and other detector measurements. A SWIR algorithm to analyze SWIR measurements may take inputs from PPG measurements, SWIR measurements and other detector measurements. Other detector biomarker algorithms to analyze other detector measurements may take inputs from PPG measurements, SWIR measurements and other detector measurements.

FIG. 9 shows that inputs from both a primary measurement and from the output of a calibration model may be input into a biomarker algorithm. For example, a PPG algorithm to analyze PPG measurements may take inputs from PPG measurements, and from the outputs of a SWIR biomarker algorithm and other detector algorithms. A SWIR algorithm to analyze SWIR measurements may take inputs from SWIR data, and from the outputs of a PPG algorithm and other detector algorithms. Other detector algorithms to analyze other detector measurements may take inputs from other detector data and from the outputs of a PPG algorithm and a SWIR algorithm.

In this way, the computer-implemented method according to the invention may increase the accuracy of biomarker value calculations which use spectral measurements that are variable with a factor external to the biomarker.

Although exemplary embodiments of a computer-implemented method have been specifically described and illustrated herein, many modifications and variations will be apparent to those skilled in the art. Accordingly, it is to be understood that a computer-implemented method constructed according to principles of this invention may be embodied other than as specifically described herein. The invention is also defined in the following claims, and equivalents thereof.

What is claimed is:

1. A computer-implemented method to improve the accuracy of a calculation of a biomarker value from a spectral measurement, the computer-implemented method comprising:
   receiving a primary spectral measurement from a primary detector,
   receiving a secondary measurement from a secondary detector, and
   calculating a value of the biomarker using a biomarker algorithm, which takes an input from the primary spectral measurement and a calibration parameter from the secondary measurement,
   wherein the secondary measurement is a secondary spectral measurement that is less variable, with the biomarker, than the primary spectral measurement, and
   wherein the method further comprises:
      generating the biomarker algorithm using a plurality of training primary spectral measurements, a respective plurality of training secondary measurements, and a respective plurality of reference biomarker value labels; or
      applying a calibration model to the secondary measurement, the calibration model taking an input from the secondary measurement, and the calibration model outputting the calibration parameter.

2. The computer-implemented method of claim 1, wherein the secondary measurement is a spectral measurement.

3. The computer-implemented method of claim 2, wherein the secondary measurement is in a different wavelength band to the primary spectral measurement.

4. The computer-implemented method of claim 2, wherein the secondary measurement is a measurement of short wavelength infrared spectral data.

5. The computer-implemented method of claim 1, wherein the calibration parameter is the secondary measurement.

6. The computer-implemented method of claim 1, wherein the primary spectral measurement includes a measurement of red wavelength spectral data and a measurement of infrared wavelength spectral data.

7. The computer-implemented method of claim 6, wherein the biomarker is oxygen saturation.

8. The computer-implemented method of claim 1, wherein the primary spectral measurement is a measurement of short wavelength infrared spectral data.

9. The computer-implemented method of claim 8, wherein the biomarker is a metabolite.

10. The computer-implemented method of claim 1, wherein the biomarker algorithm is a trained machine learning model.

11. The computer-implemented method according to claim 1, wherein the biomarker algorithm is a classification model, or a regression model, or a combination of a classification model and a regression model.

12. A device comprising a processor, the processor configured to carry out the method of claim 1.

13. The computer-implemented method of claim 1, wherein the secondary measurement is approximately constant with respect to the biomarker value, and is variable with respect to a user specific characteristic.

14. A computer-implemented method to improve the accuracy of a calculation of a biomarker value from a spectral measurement, the computer-implemented method comprising:

receiving a primary spectral measurement from a primary detector, receiving a secondary measurement from a secondary detector, and calculating a value of the biomarker using a biomarker algorithm, which takes an input from the primary spectral measurement and a calibration parameter from the secondary measurement, wherein the method further comprises:

generating the biomarker algorithm using a plurality of training primary spectral measurements, a respective plurality of training secondary measurements, and a respective plurality of reference biomarker value labels; or applying a calibration model to the secondary measurement, the calibration model taking an input from the secondary measurement, and the calibration model outputting the calibration parameter.

15. The computer-implemented method of claim 14, comprising:

applying the calibration model to the secondary measurement, the calibration model taking the input from the secondary measurement, and the calibration model outputting the calibration parameter.

16. The computer-implemented method of claim 15, wherein the calibration model is generated using a plurality of training secondary measurements and a respective plurality of calibration parameter labels, wherein the plurality of training calibration parameters are calculated using a respective plurality of training primary spectral measurements and a respective plurality of reference values of the biomarker.

17. The computer-implemented method of claim 15, wherein the calibration model is a trained machine learning model.

18. The computer-implemented method of claim 15, wherein the calibration model is a classification model, or a regression model, or a combination of a classification model and a regression model.

19. The computer-implemented method according to claim 14, further comprising:

generating the biomarker algorithm using the plurality of training primary spectral measurements, the respective plurality of training secondary measurements, and the respective plurality of reference biomarker value labels.

20. A computer-implemented method to improve the accuracy of a calculation of a biomarker value from a spectral measurement, the computer-implemented method comprising:

receiving a primary spectral measurement from a primary detector, receiving a secondary measurement from a secondary detector, and calculating a value of the biomarker using a biomarker algorithm, which takes an input from the primary spectral measurement and a calibration parameter from the secondary measurement, wherein the biomarker is temperature, and wherein the method further comprises:

generating the biomarker algorithm using a plurality of training primary spectral measurements, a respective plurality of training secondary measurements, and a respective plurality of reference biomarker value labels; or applying a calibration model to the secondary measurement, the calibration model taking an input from the secondary measurement, and the calibration model outputting the calibration parameter.

21. The computer-implemented method of claim 20, wherein the primary spectral measurement is a measurement of short wavelength infrared spectral data.

* * * * *